(12) United States Patent
Miyazawa et al.

(10) Patent No.: US 9,897,601 B2
(45) Date of Patent: Feb. 20, 2018

(54) TEST KIT

(71) Applicant: Denka Seiken Co., Ltd., Chuo-ku (JP)

(72) Inventors: Takashi Miyazawa, Gosen (JP); Yuki Shinohara, Gosen (JP)

(73) Assignee: Denka Seiken Co., Ltd, Tokyo (JP)

( * ) Notice: Subject to any disclaimer, the term of this patent is extended or adjusted under 35 U.S.C. 154(b) by 0 days.

(21) Appl. No.: 14/775,176

(22) PCT Filed: Mar. 12, 2014

(86) PCT No.: PCT/JP2014/056518
§ 371 (c)(1),
(2) Date: Sep. 11, 2015

(87) PCT Pub. No.: WO2014/142179
PCT Pub. Date: Sep. 18, 2014

(65) Prior Publication Data
US 2016/0041161 A1    Feb. 11, 2016

(30) Foreign Application Priority Data

Mar. 13, 2013  (JP) ................................. 2013-050974

(51) Int. Cl.
*B01L 3/00* (2006.01)
*G01N 33/543* (2006.01)
*G01N 33/558* (2006.01)

(52) U.S. Cl.
CPC ..... *G01N 33/54386* (2013.01); *G01N 33/558* (2013.01)

(58) Field of Classification Search
CPC .................. G01N 33/54386; G01N 33/558
See application file for complete search history.

(56) References Cited

U.S. PATENT DOCUMENTS

| 5,356,782 A | 10/1994 | Moorman et al. |
|---|---|---|
| 2002/0098512 A1 | 7/2002 | Goodell et al. |

(Continued)

FOREIGN PATENT DOCUMENTS

| JP | H04-318462 | 11/1992 |
|---|---|---|
| JP | H08-501387 | 2/1996 |

(Continued)

OTHER PUBLICATIONS

"International Application No. PCT/JP2014/056518, International Search Report dated Jun. 10, 2014", (Jun. 10, 2014), 5 pgs.

(Continued)

*Primary Examiner* — Dennis White
(74) *Attorney, Agent, or Firm* — Schwegman Lundberg & Woessner, P.A.

(57) ABSTRACT

The present invention provides a test kit capable of rapid and highly sensitive detection.
The test kit has a dropping region, which contains a portion onto which a liquid sample drops, a labeling substance holding region, at least a portion of which is connected downstream of the dropping region in the developing direction, and in which a labeling substance with a label immobilized on a substance that specifically binds with the substance to be detected is held, a developing region, which has a detection zone where the labeling substance is captured through the substance to be detected, at least a portion of which is connected downstream of the labeling substance holding region in the developing direction, and which allows the labeling substance having been made to flow out from the labeling substance holding region by the liquid sample, to develop into the detection zone, and retention inhibition means for inhibiting retention of the labeling substance in the labeling substance holding region when the liquid sample develops downstream.

16 Claims, 15 Drawing Sheets

(56) References Cited

U.S. PATENT DOCUMENTS

| | | |
|---|---|---|
| 2002/0164670 A1 | 11/2002 | Forrest |
| 2002/0192839 A1 | 12/2002 | Mink et al. |
| 2004/0019301 A1 | 1/2004 | Wong et al. |
| 2007/0004006 A1 | 1/2007 | Jung |
| 2009/0093968 A1 | 4/2009 | Kawamata et al. |
| 2009/0253219 A1 | 10/2009 | Bauer et al. |
| 2011/0076781 A1 | 3/2011 | Liu et al. |
| 2016/0033501 A1 | 2/2016 | Miyazawa et al. |

FOREIGN PATENT DOCUMENTS

| | | | |
|---|---|---|---|
| JP | 2001-021562 | | 1/2001 |
| JP | 2002-202307 | | 7/2002 |
| JP | 2003-083970 | | 3/2003 |
| JP | 2003083970 A | * | 3/2003 |
| JP | 2003-513244 | | 4/2003 |
| JP | 2007-086026 | | 4/2007 |
| JP | 2008-164520 | | 7/2008 |
| JP | 2010-156571 | | 7/2010 |
| JP | 2011-191317 | | 9/2011 |
| JP | 2012-063175 | | 3/2012 |
| JP | 2012-189346 | | 10/2012 |
| JP | 2012-524279 | | 10/2012 |
| WO | WO-2003/085402 | | 10/2003 |
| WO | WO-2008/016268 A1 | | 2/2008 |
| WO | WO-2009/123592 A1 | | 10/2009 |
| WO | WO-2011/057025 A2 | | 5/2011 |
| WO | WO-2012012500 A1 | | 1/2012 |
| WO | WO-2014/142179 | | 9/2014 |
| WO | WO-2014/142181 | | 9/2014 |

OTHER PUBLICATIONS

International Application No. PCT/JP2014/056520, International Search Report dated Jun. 17, 2014, (Jun. 17, 2014), 5 pgs.

"U.S. Appl. No. 14/775,209, Non Final Office Action dated Mar. 10, 2016", 18 pgs.

"U.S. Appl. No. 14/775,209, Response filed Jun. 2, 2016 to Non Final Office Action dated Mar. 10, 2016", 9 pgs.

"U.S. Appl. No. 14/775,209 Examiner Interview Summary dated Nov. 17, 2016", 5 pgs.

"U.S. Appl. No. 14/775,209, Advisory Action dated Dec. 9, 2016", 4 pgs.

"U.S. Appl. No. 14/775,209, Final Office Action dated Sep. 16, 2016", 24 pgs.

"U.S. Appl. No. 14/775,209, Response filed Nov. 16, 2016 to Frinal Office Action dated Sep. 16, 2016", 9 pgs.

"European Application No. 14764277.1, Extended European Search Report dated Sep. 30, 2016", 9 pgs.

"European Application No. 14764552.7, Extended European Search Report dated Sep. 30, 2016", 7 pgs.

U.S. Appl. No. 14/775,209, Response filed Dec. 16, 2016 to Advisory Action dated Dec. 9, 2016, 9 pgs.

"U.S. Appl. No. 14/775,209, Non Final Office Action dated Jul. 10, 2017", 33 pgs.

\* cited by examiner

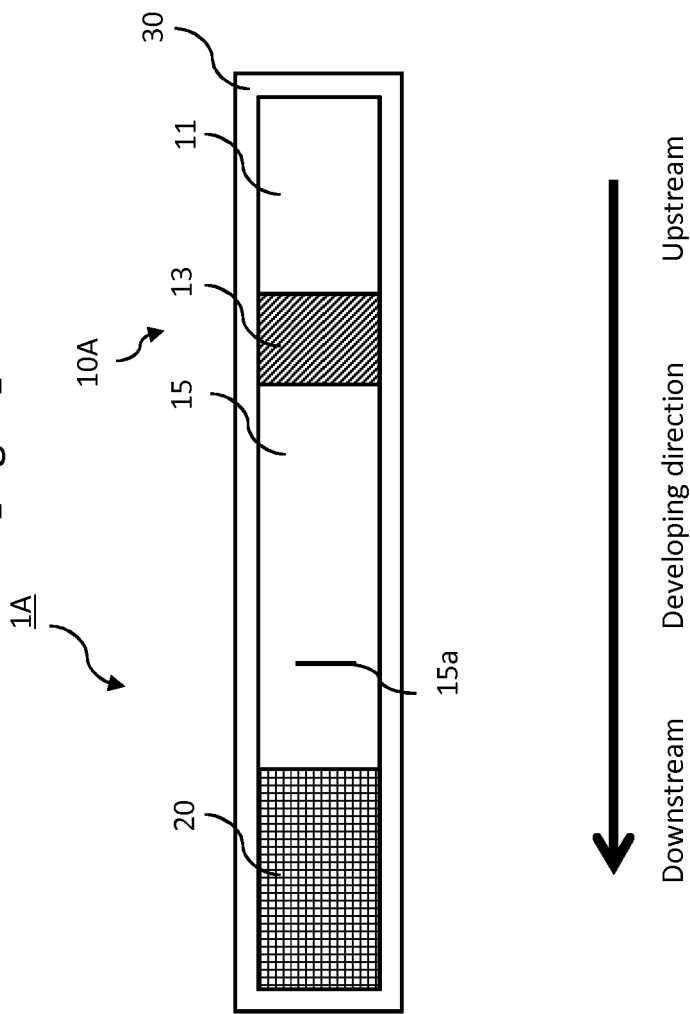

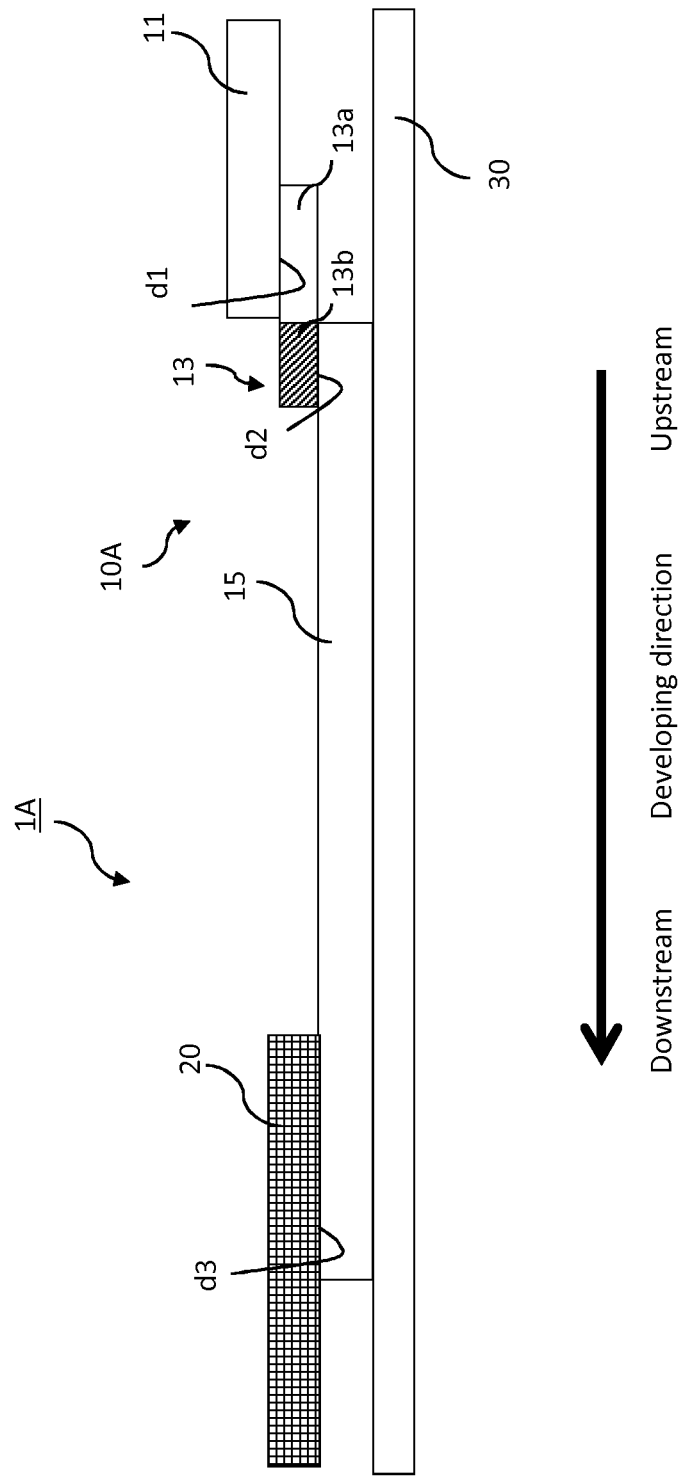

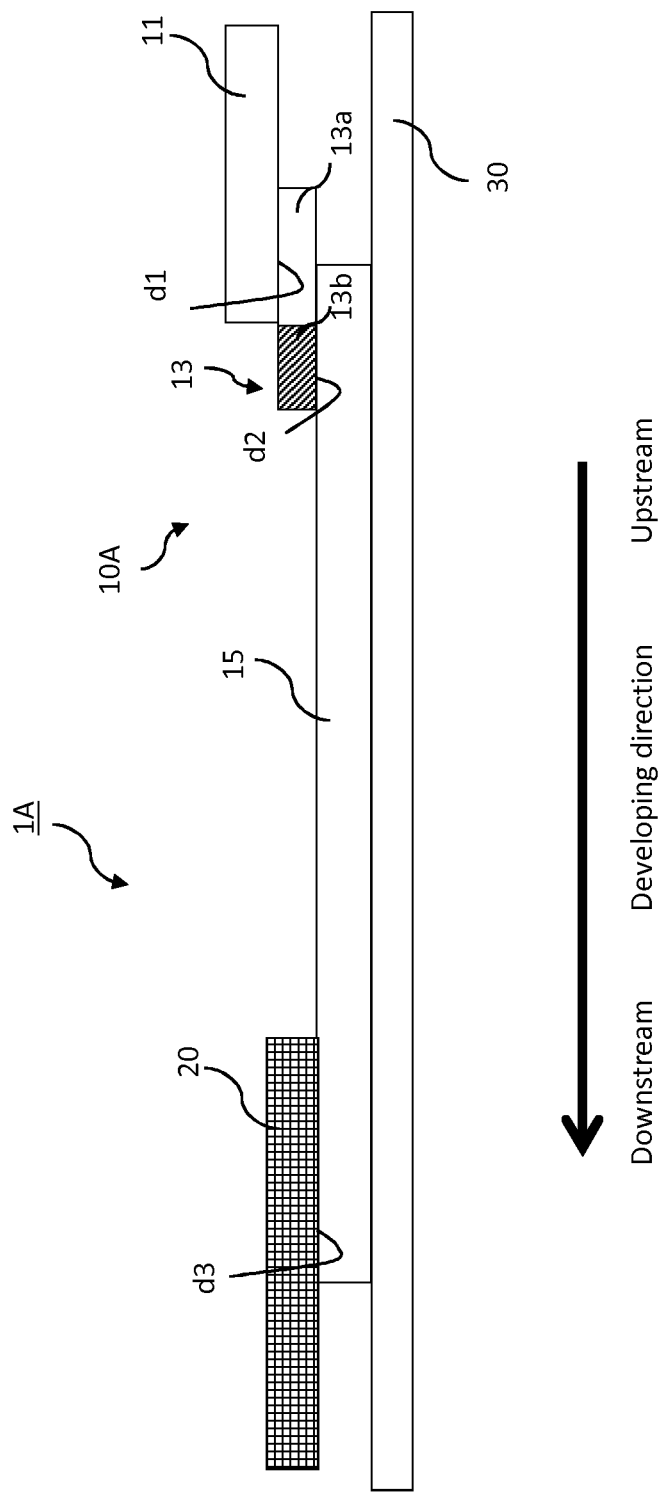
[Fig. 3]

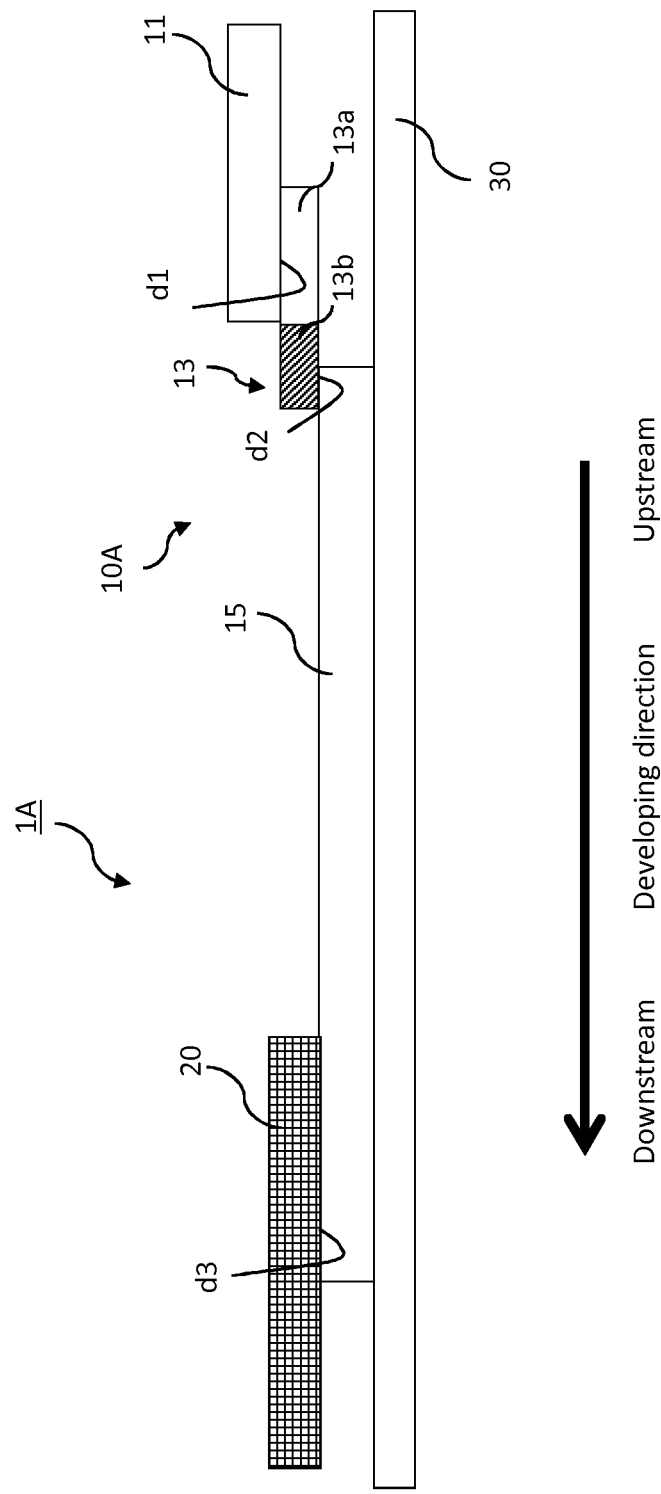

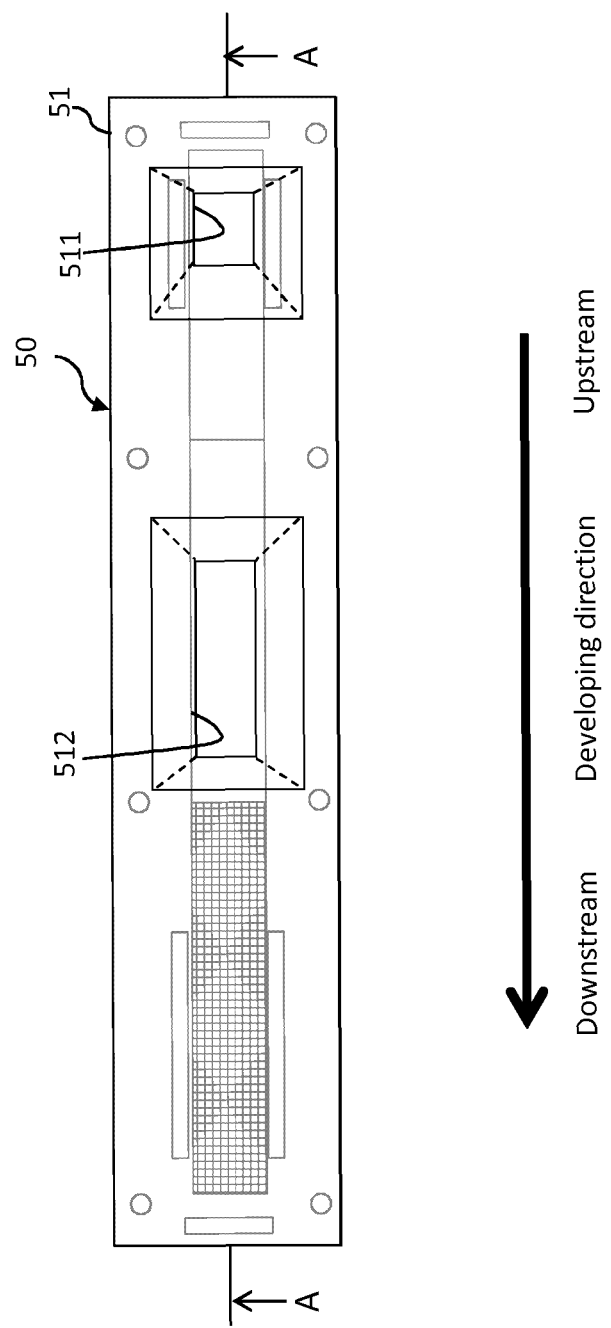

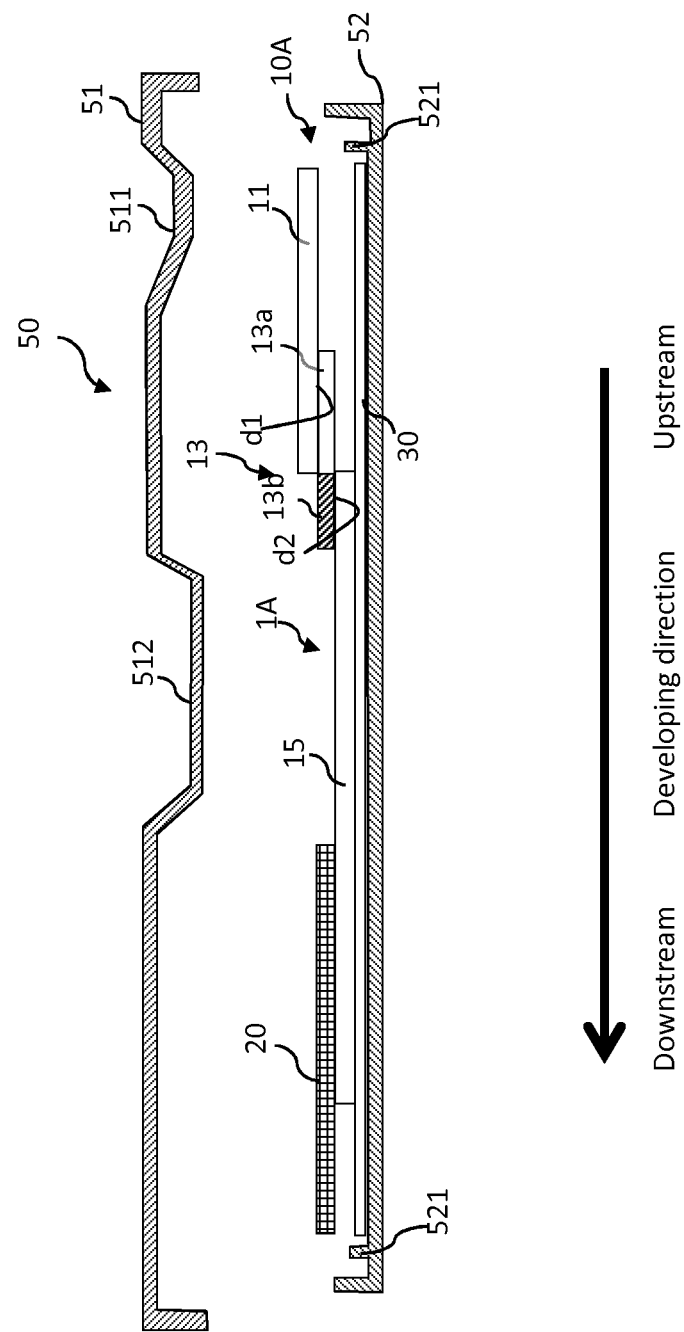
[Fig. 6]

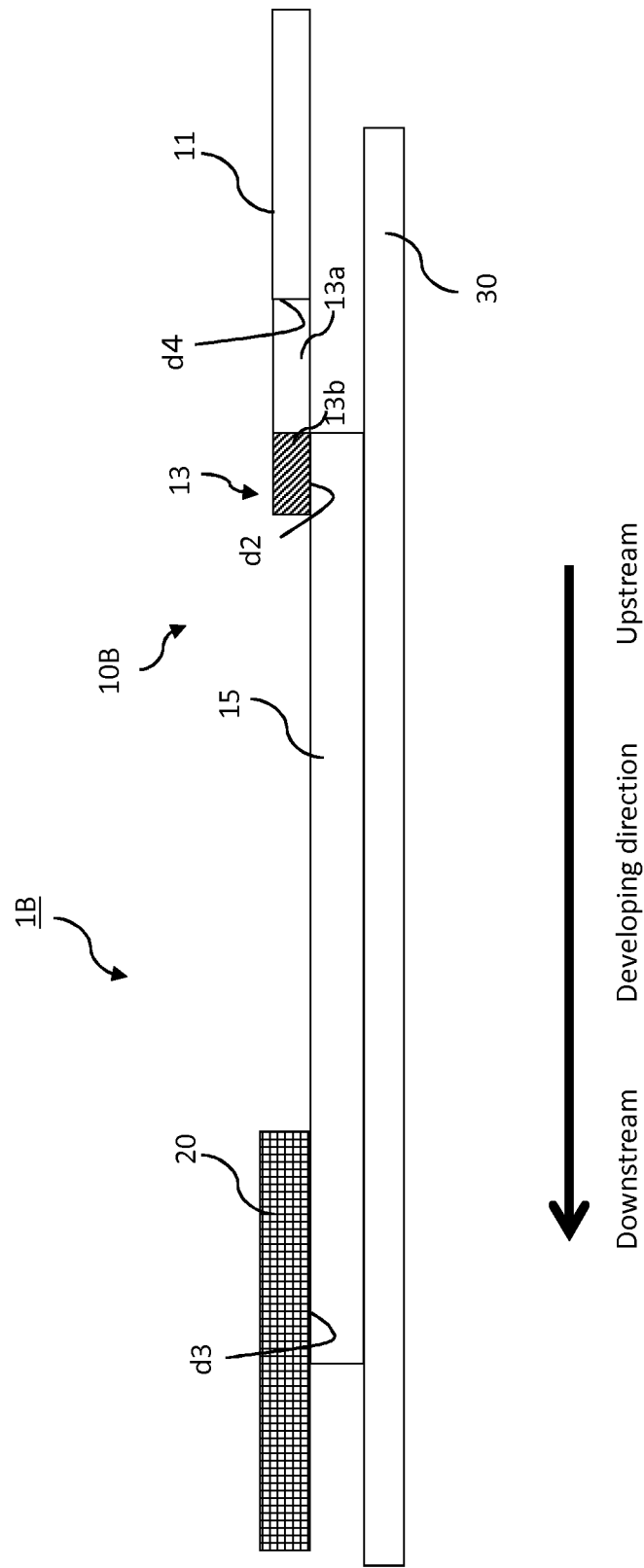

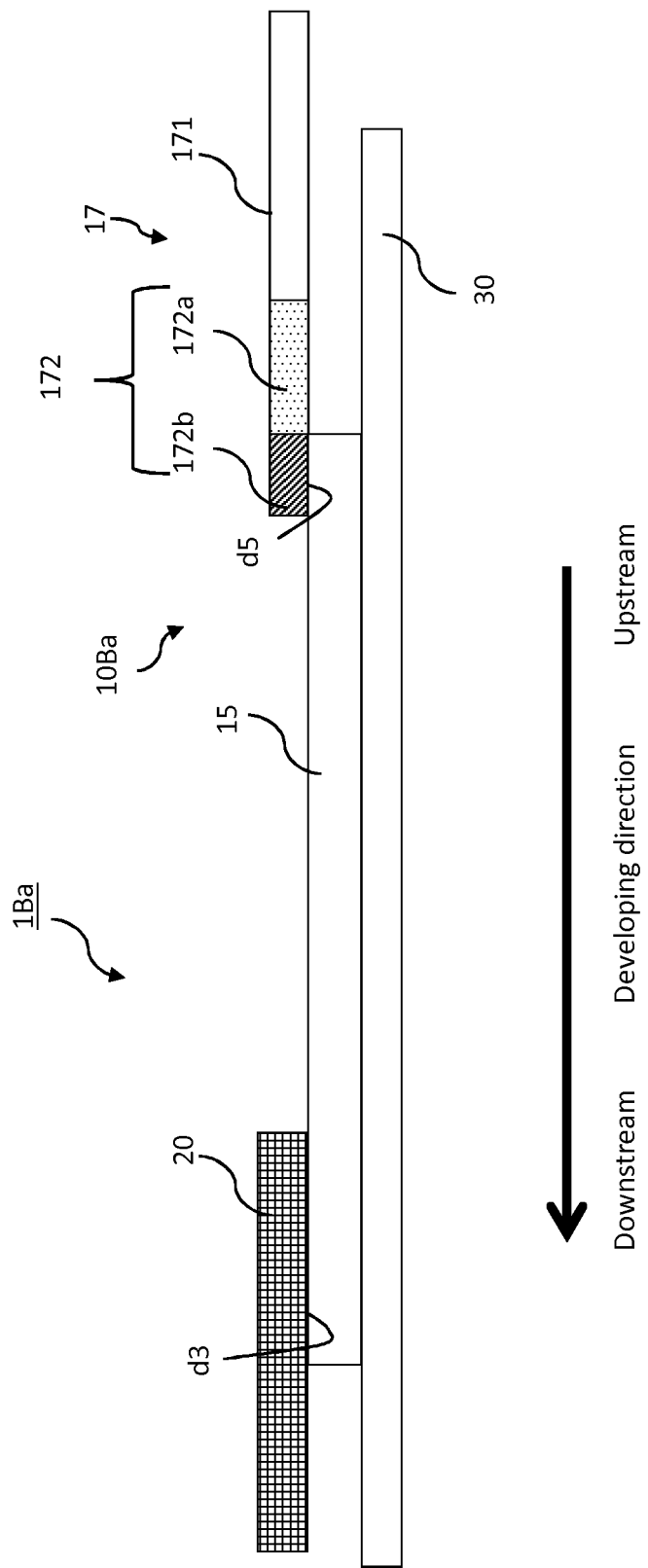

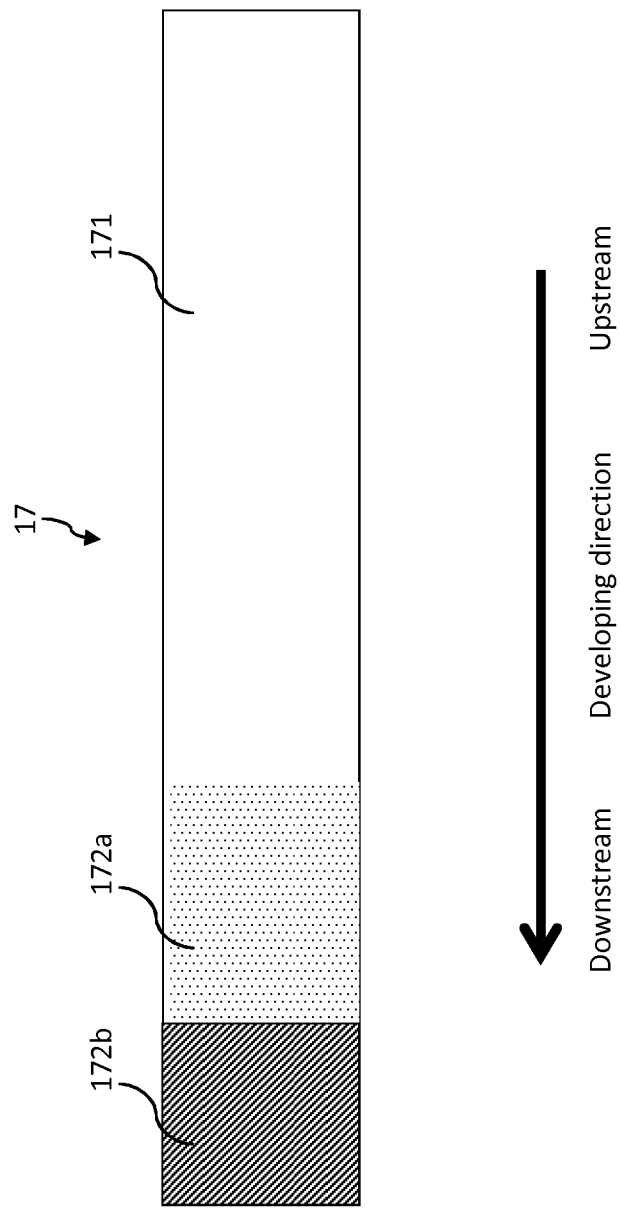

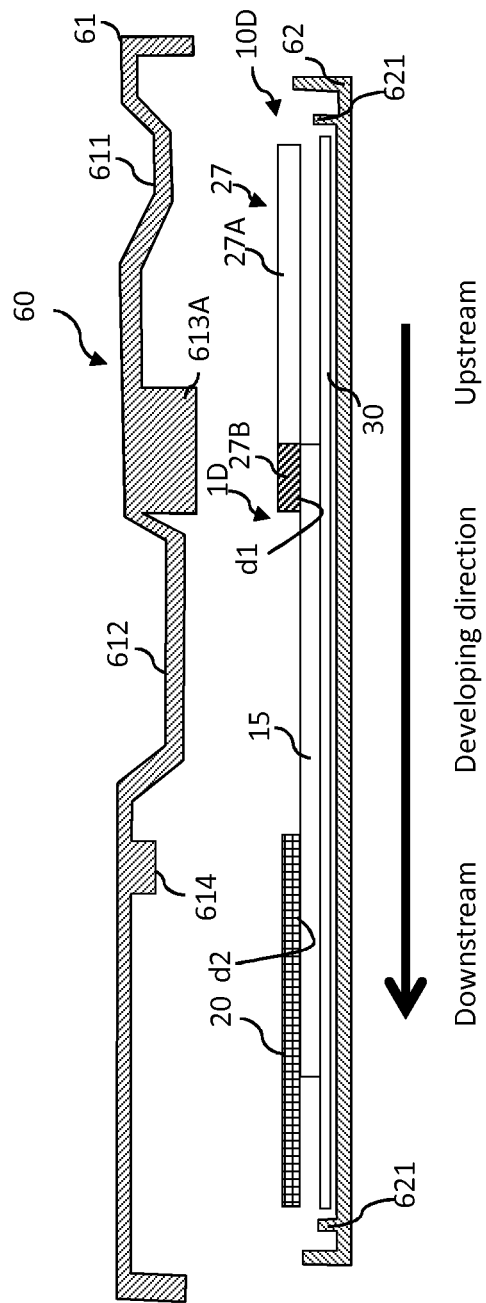

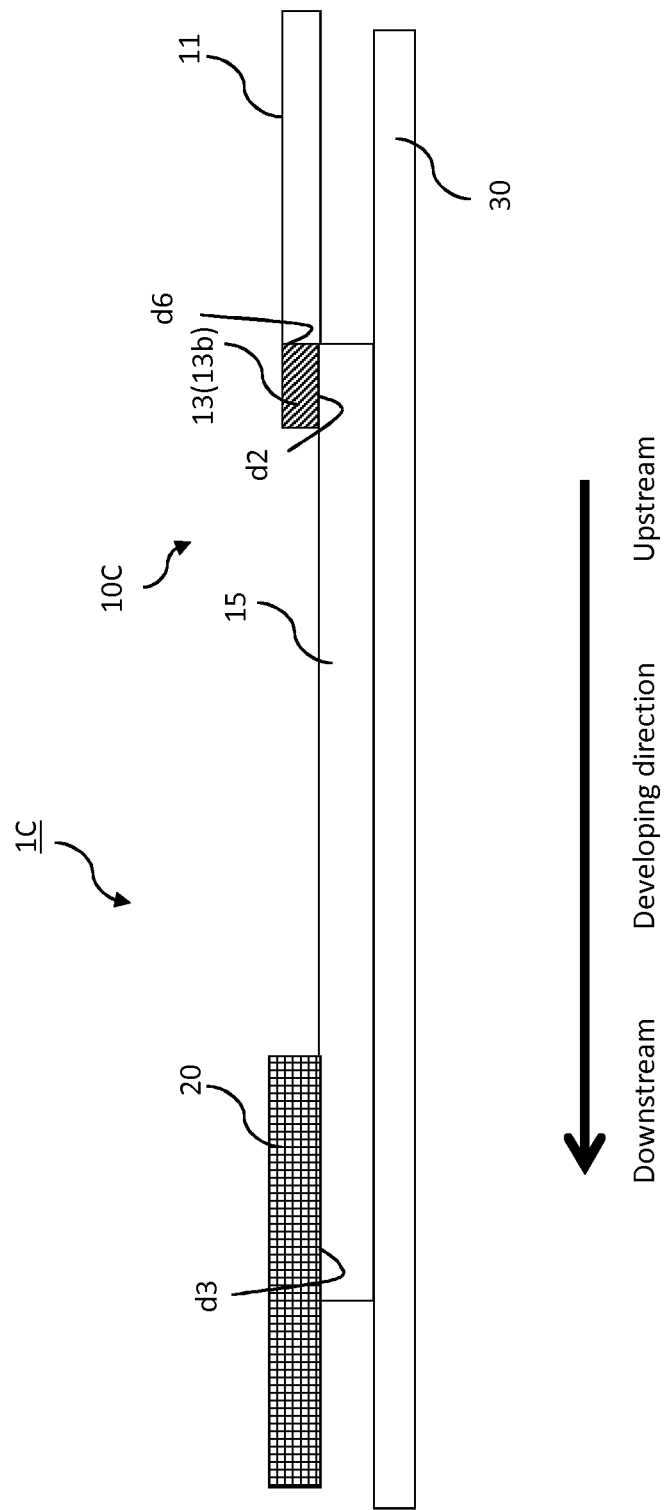
[Fig. 11]

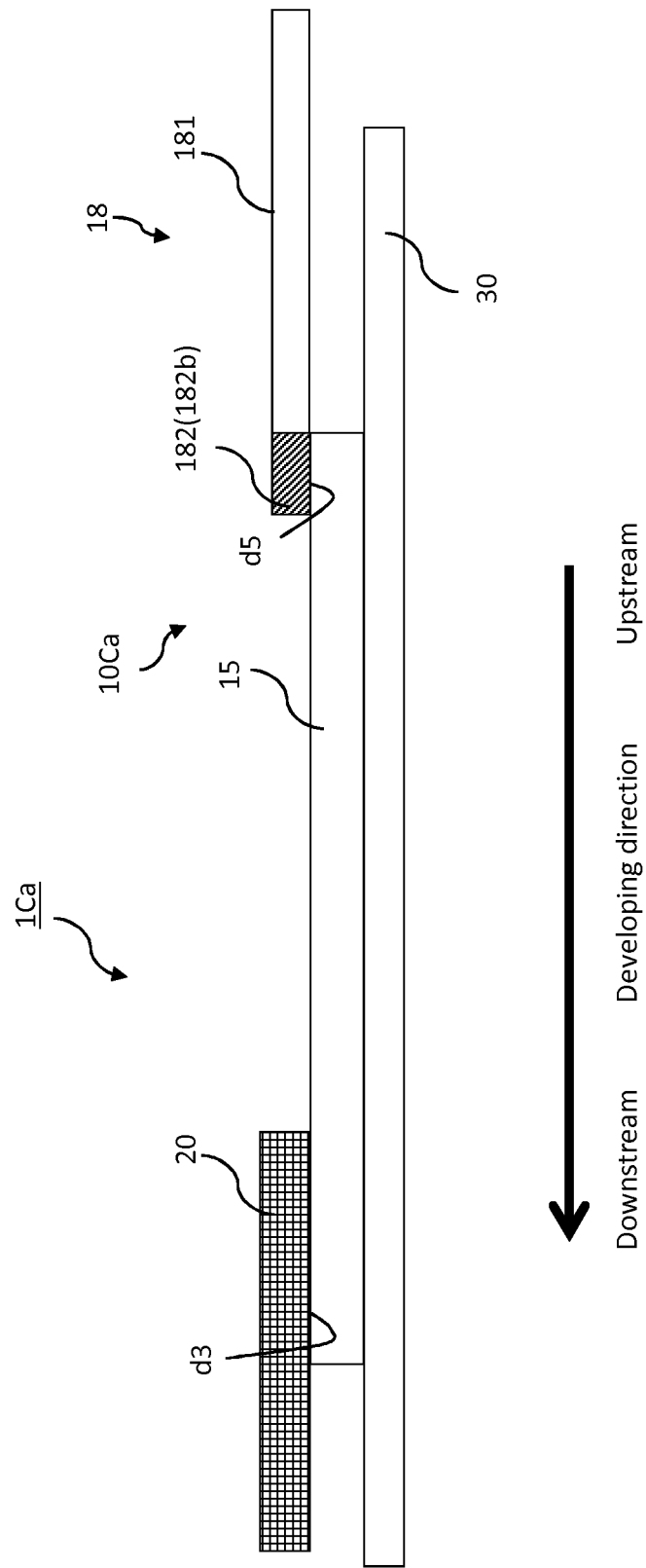
[Fig. 12]

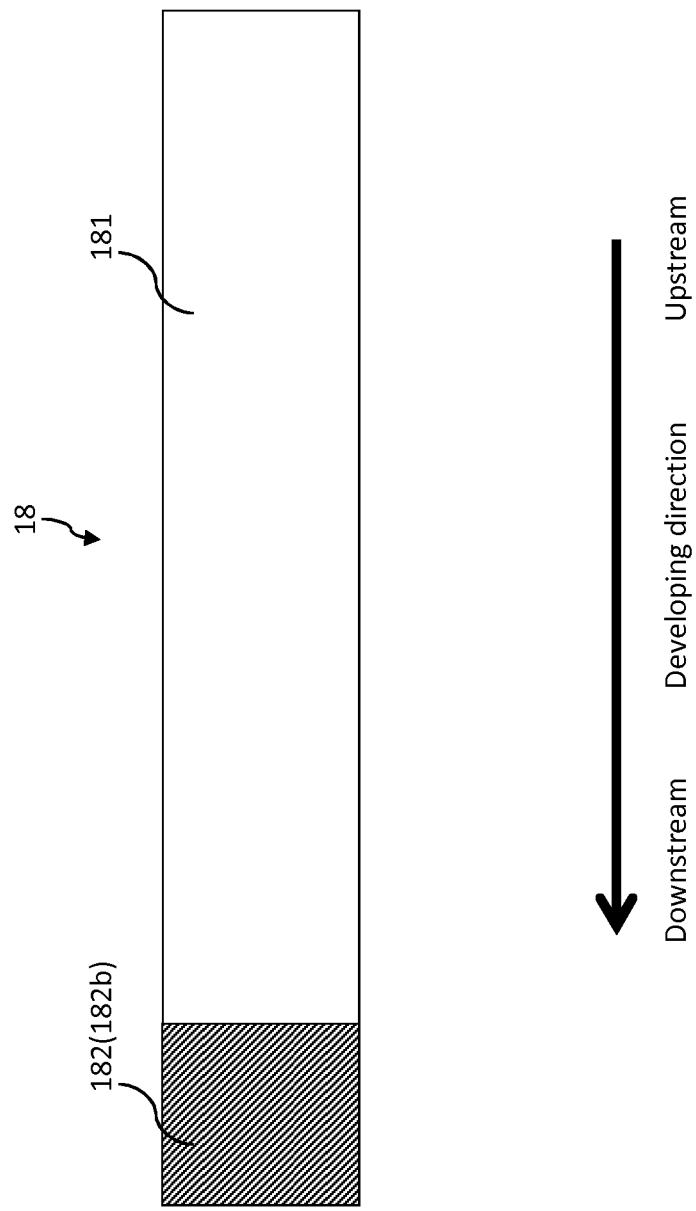

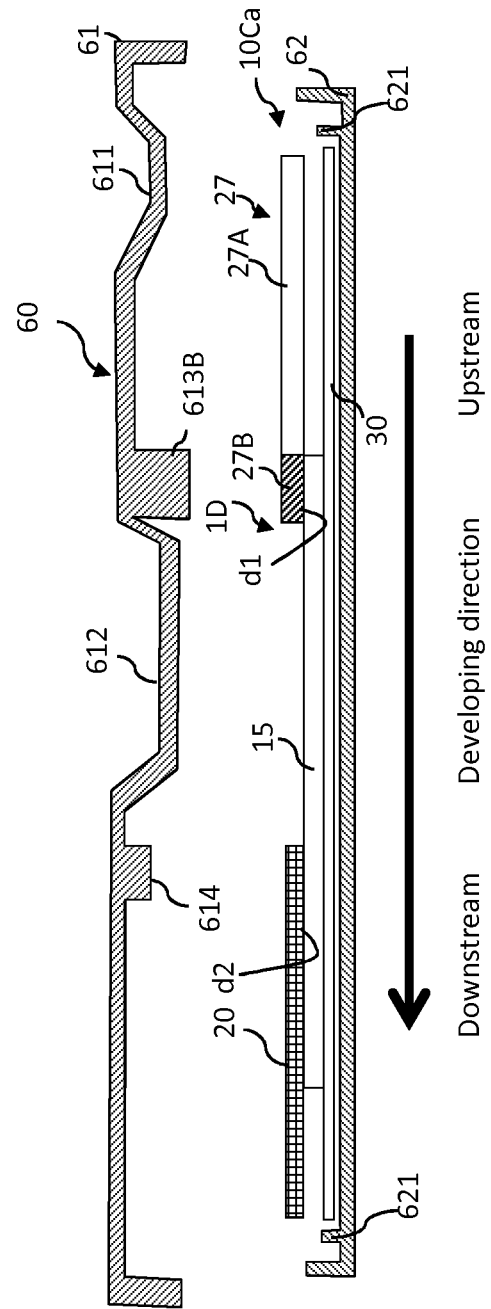

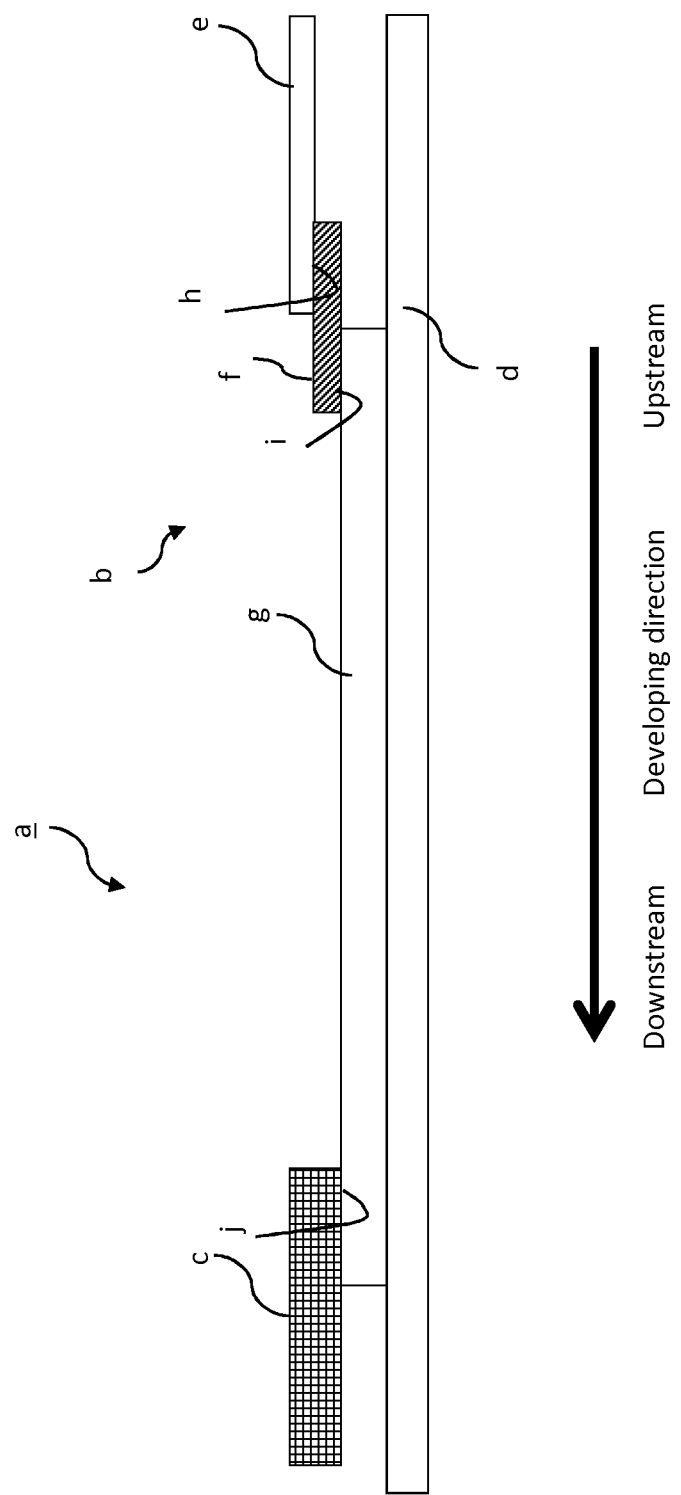

TEST KIT

PRIORITY CLAIM TO RELATED APPLICATIONS

This application is a U.S. national stage application filed under 35 U.S.C. § 371 from International Application Ser. No. PCT/JP2014/056518, which was filed 12 Mar. 2014, and published as WO2014/142179 on 18 Sep. 2014, and which claims priority to Japanese Application No. 2013-05097, filed 13 Mar. 2013, which applications and publication are incorporated by reference as if reproduced herein and made a part hereof in their entirety, and the benefit of priority of each of which is claimed herein.

TECHNICAL FIELD

The present invention relates to a test kit that uses immunochromatography.

BACKGROUND ART

Immunochromatography is a known example of an immunoassay method that detects a specific substance to be detected using an antigen-antibody or other specific reaction.

Immunochromatography is a testing method widely used as a Point Of Care Test (POCT). POCT are performed near the patient instead of sending the patient's specimen to a testing facility so as to enable the physician to rapidly assess the test results and promptly initiate treatment. Immunochromatography is used to diagnose infections derived from bacteria and viruses, and particularly infections in cases involving newborns or the elderly having diminished immune strength that require immediate treatment, and is required to demonstrate rapid and highly sensitive detection.

Simple test kits are used for assays based on immunochromatography (see PTL 1). Test kits are kits that consist of (1) allowing a liquid sample to develop downstream by capillary phenomenon, and (2) detecting a substance to be detected in the sample. Whether or not the substance to be detected is contained in the liquid sample is determined by whether or not a test line provided downstream of the liquid sample in the direction of development is labeled.

FIG. 15 is a side view of a test kit of the prior art that uses immunochromatography. A test kit a has a kit body b, which detects a substance to be detected by developing a liquid sample, an absorbent pad c, which takes up the liquid sample downstream of the kit body b, and a sheet d on which the kit body b and the absorbent pad c are installed. The kit body b has a plurality of members, and more specifically, a liquid dropping pad e, a labeling substance holding pad f and an immobilizing membrane g. At least some of these members e through g are mutually connected to allow development of the liquid sample. The following provides an explanation of each member of the kit body b.

The sample dropping pad e is a pad for dropping the liquid sample.

The labeling substance holding pad f is a pad in which the labeling substance is uniformly held. The labeling substance holding pad f is fabricated by impregnating a pad with a solution containing the labeling substance followed by drying. Furthermore, the labeling substance referred to here refers to a substance in which a first substance (antibody or antigen), which specifically binds with a substance to be detected (antigen or antibody) in the liquid sample, is immobilized on insoluble carrier particles, an enzyme-labeled ligand or a fluorescence-labeled ligand serving as a label.

The immobilizing membrane g is a pad on which a second substance (antibody or antigen), which specifically binds with a substance to be detected in the liquid sample, is immobilized in the form of a line.

The following indicates a typical procedure performed when using the above-mentioned test kit a.

When a liquid sample is dropped onto the sample dropping pad e, the liquid sample develops through the liquid dropping pad e and flows into the labeling substance holding pad f through an interface h with the labeling substance holding pad f. In the labeling substance holding pad f, the uniformly held labeling substance is made to flow out by the liquid sample and flow into the immobilizing membrane g together with the liquid sample through an interface i with the immobilizing membrane g. Moreover, the liquid sample develops through the immobilizing membrane g and is absorbed by the absorbent pad c through an interface j with the absorbent pad c.

In the above-mentioned procedure, in the case a substance to be detected is contained in the liquid sample, the substance to be detected binds with the first substance of the labeling substance. The second substance immobilized in the form of a line on the immobilizing membrane g becomes an immobilized sample, and the substance to be detected having a labeling substance bound thereto binds therewith and is captured in the form of line. As a result, since the labeling substance is captured in the form of a line, it can be confirmed by viewing the labeled test line and the substance to be detected in the sample is detected.

CITATION LIST

Patent Literature

[PTL 1]
Japanese Patent Application Publication No. 2002-202307

SUMMARY OF INVENTION

Technical Problem

Test kits using immunochromatography are required to demonstrate rapid and highly sensitive detection. Thus, it is necessary that a labeling substance holding pad be allowed to develop to the location of a test line on an immobilizing membrane as rapidly as possible, and that the labeling substance be reliably developed so as not to remain in the vicinity of the test line in order to facilitate identification of the test line.

However, rapid and reliable development may be inhibited as a result of the labeling substance ending up being retained in the labeling substance holding pad.

Thus, an object of the present invention is to provide a test kit that enables rapid and highly sensitive detection.

Solution to Problem

The test kit is a kit for detecting a substance to be detected contained in a liquid sample by allowing the liquid sample to develop in a developing direction, and has a dropping region, which contains a portion onto which the liquid sample drops; a labeling substance holding region, at least a portion of which is connected downstream of the dropping region in the developing direction, and in which a labeling substance with a label immobilized on a substance that specifically binds with the substance to be detected is held; a developing region, which has a detection zone where the labeling substance is captured through the substance to be detected, at least a portion of which is connected downstream of the labeling substance holding region in the developing direction, and which allows the labeling substance having been made to flow out from the labeling substance holding region by the liquid sample, to develop into the detection zone; and retention inhibition means for inhibiting retention of the labeling substance in the labeling substance holding region when the liquid sample develops downstream.

The test kit further has backflow inhibiting means for inhibiting the liquid sample containing the labeling substance from flowing back from a downstream region in the developing direction to an adjacent upstream region in the developing direction.

In the backflow inhibiting means, the absorbency of the downstream region in the developing direction may be set higher than the absorbency of the upstream region in the developing direction.

The backflow inhibiting means may be provided between the labeling substance holding region and the dropping region.

The retention inhibiting means is configured such that a non-containing portion not containing the labeling substance is arranged in a furthermost upstream portion of the labeling substance holding region where absorbency is uniform.

The retention inhibiting means is configured such that the dropping region is further connected only to the non-containing portion.

The retention inhibiting means is configured such that an end surface of the dropping region on the downstream side is further connected to an end surface of the non-containing portion on the upstream side.

The dropping region and the labeling substance holding region may be integrally formed by a single member.

The single member may be a fibrous member having uniform absorbency, and the labeling substance holding region may be formed by pressing a portion serving as the labeling substance holding region.

The retention inhibiting means is configured such that an end surface of the dropping region on the downstream side is connected to an end surface of the labeling substance holding region on the upstream side.

The dropping region and the labeling substance holding region may be integrally formed by a single member.

The single member may be a fibrous member having uniform absorbency, and the labeling substance holding region may be formed by pressing a portion serving as the labeling substance holding region.

The test kit has a dropping region, which contains a portion onto which a liquid sample drops; a labeling substance holding region, at least a portion of which is connected downstream of the dropping region in the developing direction, and in which a labeling substance with a label immobilized on a substance that specifically binds with the substance to be detected is held; and a developing region, which has a detection zone where the labeling substance is captured through the substance to be detected, at least a portion of which is connected downstream of the labeling substance holding region in the developing direction, and which allows the labeling substance having been made to flow out from the labeling substance holding region by the liquid sample, to develop into the detection zone. Moreover, the absorbency of the labeling substance holding region is set higher than the absorbency of the dropping region, and a non-containing portion that does not contain the labeling substance is provided in a furthermost upstream portion of the labeling substance holding region.

The test kit has a dropping region, which contains a portion onto which a liquid sample drops; a labeling substance holding region, at least a portion of which is connected downstream of the dropping region in the developing direction, and which is formed of only a region in which a labeling substance with a label immobilized on a substance that specifically binds with the substance to be detected is held; and a developing region, which has a detection zone where the labeling substance is captured through the substance to be detected, at least a portion of which is connected downstream of the labeling substance holding region in the developing direction, and which allows the labeling substance having been made to flow out from the labeling substance holding region by the liquid sample, to develop into the detection zone. Moreover, the absorbency of the labeling substance holding region is set higher than the absorbency of the dropping region, and an end surface of the dropping region on the downstream side is connected to an end surface of the labeling substance holding region on the upstream side.

Advantageous Effects of Invention

According to the present invention, detection can be carried out rapidly and with high sensitivity.

BRIEF DESCRIPTION OF DRAWINGS

FIG. 1 is an overhead view showing one example of a test kit according to a first embodiment.

FIG. 2 is a side view of the test kit of FIG. 1.

FIG. 3 is a side view for explaining the arrangement of an immobilizing membrane and a labeling substance holding pad.

FIG. 4 is a side view for explaining the arrangement of an immobilizing membrane and a labeling substance holding pad.

FIG. 5 is an overhead view showing one example of a case that houses a test kit.

FIG. 6 is a cross-sectional view taken along line A-A of FIG. 5.

FIG. 7 is an overhead view showing one example of a test kit according to a second embodiment.

FIG. 8 is an overhead view showing a variation of a test kit according to a second embodiment.

FIG. 9 is an overhead view of a first pad of FIG. 8.

FIG. 10 is a drawing for explaining another variation of a test kit according to a second embodiment.

FIG. 11 is an overhead view showing one example of a test kit according to a third embodiment.

FIG. 12 is an overhead view showing a variation of a test kit according to a third embodiment.

FIG. 13 is an overhead view of a second pad of FIG. 12.

FIG. 14 is a drawing for explaining another variation of a test kit according to a third embodiment.

FIG. 15 is an overhead view showing a test kit of the prior art.

DESCRIPTION OF EMBODIMENTS

The following provides an explanation of several embodiments of the present invention with reference to the drawings. Furthermore, in the following explanations, duplicate explanations of those portions that have the same structural portions and are indicated with the same reference symbols are omitted as a general rule since they carry out the same operation.

<<First Embodiment>>

FIG. 1 is an overhead view showing one example of a test kit 1A according to a first embodiment. FIG. 2 is a side view of the test kit 1A of FIG. 1. The following provides an explanation of the test kit 1A according to the first embodiment with reference to the drawings.

<Configuration of Test Kit>

The test kit 1A is a kit that detects a substance to be detected (antibody or antigen, to apply similarly hereinafter) contained in a liquid sample by allowing the liquid sample to develop in a developing direction (which may be hereinafter simply referred to as the developing direction). More specifically, whether or not a substance to be detected is contained in a liquid sample is determined according to whether or not a test line, which is provided downstream of the liquid sample dropped onto the test kit 1A, is labeled. The developing direction of the liquid sample is indicated with an arrow in the drawings.

The test kit 1A has a kit body 10A, an absorbent pad 20 and a sheet 30. The sheet 30 is, for example, waterproof, and the upper surface thereof may be a widely known adhesive sheet. The kit body 10A and the absorbent pad 20 are connected and arranged on the upper surface of the sheet 30. The kit body 10A allows determination of the presence or absence of a substance to be detected (antigen or antibody, to apply similarly hereinafter) by developing a liquid sample. The absorbent pad 20 takes up liquid sample that has been developed by the kit body 10A.

<Explanation of Each Member>

The kit body 10A has a dropping region in the form of a sample dropping pad 11, a labeling substance holding region in the form of a labeling substance holding pad 13, and a developing region in the form of an immobilizing membrane 15.

The sample dropping pad 11 is arranged furthermost upstream in the developing direction. The sample dropping pad 11 has a dropping portion (not shown) onto which a liquid sample is dropped. The sample dropping pad 11 has a prescribed water absorbency. More specifically, the sample dropping pad 11 is formed with a fibrous member having comparatively low absorbency. In addition, the sample dropping pad 11 is formed with a fibrous member having comparatively coarse openings and a rapid liquid developing speed.

At least a portion of the labeling substance holding pad 13 is connected downstream of the sample dropping pad 11 in the developing direction. More specifically, the end portion on the upstream side of the labeling substance holding pad 13 in the developing direction is arranged superimposed below the end portion of the downstream side of the sample dropping pad 11 in the developing direction. As a result, an interface d1 is formed by the upper surface of the labeling substance holding pad 13 and the lower surface of the sample dropping pad 11. The labeling substance holding pad 13 has higher water absorbency and slower liquid developing speed than the sample dropping pad 11. For example, the labeling substance holding pad 13 is formed with a fibrous member having finer openings than those of the sample dropping pad 11. In addition, absorbency of the labeling substance holding pad 13 is uniform. A liquid sample is absorbed through the interface d1 by the labeling substance holding pad 13 at a stronger force than that during development by the sample dropping pad 11.

A labeling substance is held in the labeling substance holding pad 13. The labeling substance holding pad 13 has a non-containing portion 13a that does not contain a labeling substance, and a containing portion 13b that contains the labeling substance. Furthermore, the interface d1 may be formed by joining the lower surface of the sample dropping pad 11 to the entire surface of the upper surface of the non-containing portion 13a as shown in the figure, or may be formed by joining a portion of the upper surface of the non-containing portion 13a to the lower surface of the sample dropping pad 11.

Although a labeling substance may be uniformly held in the containing portion 13b, for example, it is not limited thereto. Here, the labeling substance refers to a substance in which a substance that specifically binds to a substance (antibody or antigen, to apply similarly hereinafter) to be detected in a liquid sample is immobilized on insoluble carrier particles, an enzyme-labeled ligand or a fluorescence-labeled ligand serving as a label. Examples of insoluble carrier particles serving as a label include gold colloids, platinum colloids, colored particles and fluorescent particles. The labeling substance held in the labeling substance holding pad 13 is caused to flow out by the liquid sample and develop downstream together with the liquid sample. In the case a substance to be detected is contained in the liquid sample, the labeling substance specifically binds with the substance to be detected resulting in a labeled complex that develops towards the downstream side.

At least a portion of the immobilizing membrane 15 is connected downstream of the labeling substance holding pad 13 in the developing direction. More specifically, the end portion on the upstream side of the immobilizing membrane 15 in the developing direction is arranged superimposed below the end portion on the downstream side of the labeling substance holding pad 13 in the developing direction. As a result an interface d2 is formed by the upper surface of the immobilizing membrane 15 and the lower surface of the labeling substance holding pad 13. The immobilizing membrane 15 has higher absorbency and slower liquid developing speed than the labeling substance holding pad 13. For example, the immobilizing membrane 15 is formed with a fibrous member (membrane body) such as a nitrocellulose membrane that has finer openings than those of the labeling substance holding pad 13. The liquid sample is absorbed through the interface d2 by the immobilizing membrane 15 with a stronger force than that than during development of the labeling substance holding pad 13.

Furthermore, although the containing portion 13b is arranged so as to only contact the upper surface of the immobilizing membrane 15 at the interface d2 in FIG. 2, it is not limited thereto. For example, not only the containing portion 13b, but also the non-containing portion 13a may be arranged so as to contact the upper surface of immobilizing membrane 15 as shown in FIG. 3. In addition, a portion of the containing portion 13b, for example, may be arranged so as to contact the upper surface of the immobilizing membrane 15 as shown in FIG. 4.

The immobilizing membrane 15 has a region, in which a substance (antibody or antigen, to apply similarly hereinafter) that specifically binds with a substance to be detected is immobilized, in the form of a detection zone 15a (see FIG. 1). The test line is labeled as a result of the labeled complex specifically binding in the detection zone 15a and the labeling substance being captured in the form of a line. Furthermore, although not shown in the drawings, the immobilizing membrane 15 may also have a region in which a control substance (antibody or antigen, to apply similarly hereinafter) is immobilized in the form of a control zone. The control zone is preferably arranged on the downstream side of the detection zone 15a. In this case, by further holding a control labeling substance, in which insoluble carrier particles and the like for labeling have been immobilized on a substance (antigen or antibody) that specifically binds to the control substance, in the labeling substance holding pad 13, a liquid sample (which includes these labeling substances) can be confirmed to have been developed in the control zone.

The absorbent pad 20 is a pad that absorbs the liquid sample of the kit body 10. At least a portion of the absorbent pad 20 is connected downstream of the immobilizing membrane 15 in the developing direction. More specifically, the end portion on the upstream side of the absorbent pad 20 in the developing direction is placed on the end portion on the downstream side of the immobilizing membrane 15 in the developing direction. As a result, an interface d3 is formed by the upper surface of the absorbent pad 20 and the lower surface of the immobilizing membrane 15. The liquid sample is absorbed by the absorbent pad through the interface d3.

Furthermore, although portions of the sample dropping pad 11, the labeling substance holding pad 13 and the absorbent pad 20 that do not contact other members are shown in FIG. 2 (and similarly in other side views as well to be subsequently described) as being separated from the sheet 30, these portions may be adhered to the sheet 30.

In addition, the upper surface of the test kit 1A may also be made to be covered with a cover not shown made of a waterproof material. In this case, the cover may be transparent to enable viewing of the test line, and an opening may be formed in the dropping portion that allows a liquid sample to pass through.

In addition, the test kit 1A may be used by housing in a case. FIG. 5 is an overhead view showing on example of a case 50. FIG. 6 is a cross-sectional view taken along line A-A of FIG. 5.

The case 50 has a case body 52 that houses a test kit 1 and a cover 51 that covers the case body 52. A plurality of projecting portions 521 that position the test kit 1 are provided on the case body 52. An opening 511 for dropping a liquid sample onto the sample dropping region pad 11 and an opening 512 for viewing the test line on the immobilizing membrane 15 are formed in the cover 51. The test kit 1A may be housed in the case 50 while covered with a cover or the test kit 1A may be housed in the case 50 as is. Furthermore, stoppers may be provided in the cover 51 and the case 52 for locking the cover 51.

<Explanation of Each Function>

The test kit 1A is provided with a first and/or second function for rapidly and reliably developing a liquid sample. The first function is a function that inhibits a liquid sample containing a labeling substance from flowing back from a member downstream in the developing direction to an adjacent member upstream in the developing direction. More specifically, the first function is realized by a configuration in which the absorbency of the sample dropping pad 11 is lower than the absorbency of the labeling substance holding pad. As a result of employing this configuration, backflow of a liquid sample containing a labeling substance from the labeling substance holding pad 13 to the sample dropping pad 11 is inhibited. In addition, the first function is realized by a configuration in which absorbency of the labeling substance holding pad 13 is lower than the absorbency of the immobilizing membrane 15. As a result of employing this configuration, backflow of a liquid sample containing a labeling substance from the immobilizing membrane 15 to the labeling substance holding pad 13 is inhibited.

The second function is a function that inhibits a labeling substance from being retained in the labeling substance holding pad 13 when a liquid sample is developed from the labeling substance holding pad 13 to the immobilizing membrane 15. Here, retention refers to the upstream to downstream flow of a liquid sample becoming caught in a disturbance in the case that flow has been disturbed, thereby causing the flow of the labeling substance to become stagnate. Disturbances in the flow of a liquid sample can be caused by the following two events.

One of the events is the result of the liquid sample vigorously flowing into the labeling substance holding pad 13 due to the difference in absorbency between the high absorbency of the labeling substance holding pad 13 as compared with the sample dropping pad 11. The other is the result of impairment of the interface d1 per se. More specifically, since fibrous materials having openings of different sizes come in contact at the interface d1, and a minute gap is present between the two members, the liquid sample is prevented from flowing smoothly.

As was previously described, in the test kit a of the prior art, the labeling substance holding pad f was used in which a labeling substance was uniformly held throughout the entirety thereof (see FIG. 15). Consequently, there was the risk of a labeled sample being retained therein as a result of being caught in a disturbance of the flow of a liquid sample caused by flowing in from the interface h. Moreover, the lower surface of the sample dropping pad e was joined to the upper surface of the labeling substance holding pad f over a comparatively wide range. Consequently, the range over which liquid flows in from the interface h is large, the liquid sample flows into the labeling substance holding pad f with greater intensity than in the case of flowing in by gravity utilizing capillary phenomenon alone, and disturbances in the flow of the liquid sample increase, thereby causing retention of the labeling substance.

The second function is realized by a configuration in which the absorbency of the labeling substance holding pad 13 is uniform, and the non-containing portion 13a is arranged furthermost upstream therefrom. As a result of employing this configuration, in comparison with the case of using a labeling substance holding pad in which a labeling substance is uniformly held in the manner of the prior art, since the absorbencies of the furthermost upstream non-containing portion 13a and the containing portion 13b are uniform, there is little disturbance of the flow of the liquid sample in the portion where the labeling substance is present, thereby making it possible to reduce the amount of labeling substance that is retained as a result of being caught in the disturbed flow of the liquid sample. In addition, the second function is realized by a configuration in which the sample dropping pad 11 only contacts the non-containing portion 13a. At this time, the sample dropping pad 11 may be arranged at any location provided it only contacts the non-containing portion 13a (or in other words, provided the sample dropping pad 11 does not contact the containing portion 13b). As a result of arranging in this manner, the liquid sample is developed by moving to the sample dropping pad 11, the non-containing portion 13a, the containing portion 13b and the immobilizing membrane 15 in that order. Thus, since a labeling substance is not held below the interface d2 where the liquid sample flows in, retention of the labeling substance as a result of having become caught in a disturbance of the flow of the liquid sample in the vicinity of the interface d2 can be reduced.

In addition, as a result of inhibiting retention of the labeling substance, the labeling substance is able to flow from the containing portion 13b to the immobilizing membrane 15 more rapidly, and since this subsequently results in the flow of a liquid sample in which hardly any of the labeling substance is contained therein, it is difficult for the labeling substance to remain.

<Behavior within Test Kit>

The following provides a brief explanation of behavior within the test kit 1A resulting from the dropping of a liquid sample.

As was previously described, the order of absorbency of each member of the kit body 10A is such that absorbency of the immobilizing membrane 15 is highest followed by the labeling substance holding pad 13 and the sample dropping pad 11 in that order. As a result of arranging these members in the manner previously described, a liquid sample dropped into the sample dropping pad 11 of the test kit 1A flows in the manner described below.

The liquid sample develops through the sample dropping pad 11 and is absorbed through the interface d1 by the labeling substance holding pad 13 at a higher absorbency than that of development of the liquid sample through the dropping pad 11. At this time, due to the second function, the liquid sample flows into the non-contained portion 13a, the flow thereof is rectified in the non-containing portion 13a, and the liquid sample gently flows from the non-containing portion 13a towards the containing portion 13b while causing the labeling substance held in the containing portion 13b to flow out.

After having flown out from the containing portion 13b, the labeling substance is absorbed through the interface d2 by the immobilizing membrane 15 together with the liquid sample with a force (absorbency) that is stronger than that when developing through the labeling substance holding pad 13. At this time, liquid sample remaining in the non-containing portion 13a causes the labeling substance to flow out even after the majority of the labeling substance has flown out from the containing portion 13b.

In the case a substance to be detected is contained in the liquid sample, the labeling substance binds with the substance to be detected during development resulting in the formation of a labeled complex. Subsequently, the labeled complex binds to the immobilized sample in the detection zone 15a and is labeled in the form of a test line.

Liquid sample that has developed through the immobilizing membrane 15 is absorbed by the absorbent pad 20 after having reached the interface d3.

On the basis of the above, the test kit 1A is able to prevent the labeling substance from being caught in a disturbance of the flow of the liquid sample and inhibit retention of the labeling substance as a result of the liquid sample flowing only into the furthermost upstream non-containing portion 13a from the interface d1 and subsequently flowing into the containing portion 13b having uniform absorbency due to the second function thereof. In addition, backflow to a member on the upstream side can be prevented by the first function even in the case the labeling substance has become caught in a disturbance of the flow of the liquid sample. As a result of providing these functions, the labeling substance is able to flow into the immobilizing membrane 15 more rapidly, thereby enabling the remaining liquid sample to promote the flow of the labeling substance and making it possible to carry out detection rapidly and with high sensitivity.

<<Second Embodiment>>

FIG. 7 is an overhead view showing one example of a test kit according to a second embodiment. The following provides an explanation of one example of a test kit 1B according to the second embodiment with reference to the drawings.

At least a portion of a labeling substance holding region in the form of the labeling substance holding pad 13 is connected downstream of a dropping region in the form of the sample dropping pad 11 in the developing direction. More specifically, the end surface of an adjacent labeling substance holding pad 13 on the upstream side in the developing direction and the end surface of the sample dropping pad 11 on the downstream side in the developing direction are arranged so as to be in contact. As a result, an interface d4 is formed.

The configuration that realizes the second function according to the present embodiment consists of providing the furthermost upstream non-containing portion 13a of the labeling substance holding pad 13 in addition to connecting the end surface of the sample dropping pad 11 on the downstream side to the end surface of the non-containing portion 13a on the upstream side. Thus, since the labeling substance is not held at the location where the liquid sample flows in, the test kit 1B is able to inhibit retention of the labeling substance caused by becoming trapped in a disturbance of the flow of the liquid sample. In addition, since the end surface of the non-containing portion 13a and the end surface of the sample dropping pad 11 are connected while mutually adjacent, the test kit 1B is able to decrease the area of the interface d4 in comparison with the case of arranging the liquid dropping pad 11 superimposed on the non-containing portion 13a, and since the flow volume of the liquid sample can be decreased without being affected by gravity, disturbances in the flow of the liquid sample are suppressed and retention of the labeling substance can be further inhibited.

In the above-mentioned description, the end surface of the labeling substance holding pad 13 on the upstream side and the end surface of the sample dropping pad 11 on the downstream side were connected while being respectively formed with separate members. However, the labeling substance holding region and the dropping region may also be integrally formed with a single member. The following provides a detailed explanation thereof.

FIG. 8 is a side view showing a variation according to the present embodiment. FIG. 9 is an overhead view showing a first pad 17 of FIG. 8.

A kit body 10Ba has a developing region in the form of the immobilizing membrane 15 and a first pad 17. The first pad 17 is a pad in which a dropping region 171 having a prescribed absorbency and a labeling substance holding region 172 having higher absorbency than the dropping region 171 are integrally formed by a single member. The labeling substance holding region 172 has a non-containing portion 172a that does not contain a labeling substance, and a containing portion 172b in which a labeling substance is contained. Although the containing portion 172b holds, for example, the labeling substance uniformly, it is not limited thereto. The first pad 17 may be formed by pressing only the labeling substance holding region 172 so that the absorbency of the labeling substance holding region 172 is higher than that of the dropping region 171. More specifically, for example, the first pad 17 may be integrally formed by compression heating and the like so that the absorbency of the labeling substance holding region 172 is higher than that of the dropping region 171, or may be formed by integrally laminating fibers of different materials by thermal fusion bonding and the like so that the absorbency of the labeling substance holding region 172 is higher than that of the sample dropping region 171.

The test kit 1Ba is able to facilitate assembly by integrally forming the dropping region and labeling substance holding region having difference absorbencies of the first pad 17 with a single member.

FIG. 10 is a side view showing another variation according to the present embodiment.

In a test kit 1D of the present embodiment, the labeling substance holding region is formed by pressing the end portion on the downstream side in the lengthwise direction of a fibrous material having uniformly coarse openings (namely, absorbency) in the form of a first pad 27 at a desired pressure. More specifically, for example, a portion serving as a labeling substance holding region of the first pad 27 is pressed at a desired pressure by housing in a case 60. The following provides an explanation thereof.

The first pad 27 has a containing portion 27B that uniformly contains a labeling substance. The containing portion 27B is formed by impregnating one end portion of the first pad 27 in the lengthwise direction with a solution containing the labeling substance followed by drying. Furthermore, the labeling substance is not held in a region 27A constituting a region other than the containing portion 27B of the first pad 27 (which hereinafter may also be referred to as non-containing region 27A).

The case 60 has a case body 62 that houses the test kit 1D and a cover 61 that covers the case body 62. For example, a plurality of projecting portions 621 for positioning the test kit 1 are provided rising from the case body 62. An opening 611 for dropping a liquid sample onto the sample dropping region 171 and an opening 612 for viewing a test line on the immobilizing membrane 15 are formed in the cover 61. A pressing portion 613A for forming the labeling substance holding region on the first pad 27 is formed in the cover 61. The pressing portion 613A is provided at a location that opposes the end portion on the downstream side of the first pad 27 (and more specifically, the containing portion 27B and a portion on the downstream side of the non-containing portion 27A), with the test kit 1D housed in the case 60. Thus, in the case the test kit 1D having the first pad 27 is housed in the case body 62, fibers of the end portion on the downstream side of the first pad 27 are crushed by the pressing portion 613A, thereby enabling the formation of a difference in the absorbency of the first pad 27, and resulting in the formation of a sample dropping region and a labeling substance holding region having a higher absorbency than the sample dropping region.

In the above-mentioned embodiment, as a result of providing the pressing portion 613A in the case 60, production can be simplified without having to process the first pad 27 prior to incorporating in the case 60. Furthermore, a projection 614 may also be provided in the cover 61 for pressing the downstream side of the immobilizing membrane 15 (for example, in the vicinity of the interface d2 between the absorbent pad 20 and the immobilizing membrane 15 farther downstream than the location of the test line). As a result, fibers on the downstream side of the immobilizing membrane 15 are crushed and the liquid sample is able to flow smoothly.

In addition, although the pressing portion 613A was formed in the cover 61 of the case 60 in the above-mentioned description, it is not limited thereto. For example, a pressing portion may be formed protruding from the bottom of the case body 62. Moreover, restraining members and the like may be used that use a prescribed pressing force to restrain the end portion on the downstream side of the first pad 27 from above and below instead of using the case 60.

<<Third Embodiment>>

FIG. 11 is an overhead view showing one example of a test kit according to a third embodiment. The following provides an explanation of one example of a test kit 1C according to the third embodiment with reference to the drawings.

In the present embodiment, the labeling substance holding pad 13 does not contain a non-containing portion and is formed with only the containing portion 13b. Although the containing portion 13b holds, for example, the labeling substance uniformly, it is not limited thereto and is not required to hold the labeling substance uniformly.

At least a portion of the labeling substance holding pad 13 is connected downstream of a dropping region in the form of the sample dropping pad 11 in the developing direction. More specifically, the end surface of an adjacent labeling substance holding pad 13 on the upstream side in the developing direction and the end surface of the sample dropping pad 11 on the downstream side in the developing direction are connected. As a result, an interface d6 is formed.

The second function according to the present embodiment is realized by a configuration in which the end surface of the sample dropping pad 11 on the downstream side is connected to the end surface of the labeling substance holding pad 13 (namely, the containing portion 13b) on the upstream side. Thus, in the test kit 1C, as a result of arranging the end surface of the labeling substance holding pad 13 and the end surface of the sample dropping pad 11 in mutual adjacency, the area of the interface thereof can be decreased in comparison with the case of arranging the sample dropping pad 11 superimposed on the labeling substance holding pad 13, thereby making it possible to decrease the flow volume of the liquid sample, suppress disturbances in the flow of the liquid sample without being affected by gravity, and inhibit retention of the labeling substance caused by becoming caught in a disturbance of the flow of the liquid sample.

In the above-mentioned description, the end surface of the labeling substance holding pad 13 on the upstream side and the end surface of the sample dropping pad 11 on the downstream side were connected. However, the labeling substance holding region and the dropping region may also be integrally formed by a single member. The following provides a detailed description thereof.

FIG. 12 is a side view showing a variation according to the present embodiment. FIG. 13 is an overhead view showing a second pad 18 of FIG. 12.

A test kit 10Ca has a developing region in the form of the immobilizing membrane 15 and the second pad 18. The second pad 18 is a pad in which a dropping region 181, having a prescribed absorbency and a labeling substance holding region 182 having higher absorbency than the dropping region 181, have been integrally formed. The labeling substance holding region 182 does not have a non-containing portion, and is formed with only a containing portion 182b. Although the containing portion 182b holds, for example, the labeling substance uniformly, it is not limited thereto. The second pad 18 may be formed by pressing only the labeling substance holding region 182 so that the absorbency of the labeling substance holding region 182 is higher than the dropping region 181. More specifically, for example, the second pad 18 may also be integrally formed by compression heating and the like so that the absorbency of the labeling substance holding region 182 is higher than that of the dropping region 181, or may be integrally formed by laminating fibers of different materials by thermal fusion bonding and the like so that the absorbency of the labeling substance holding region 182 is higher than that of the dropping region 181.

The test kit 1Ca is able to simplify production by integrally forming the second pad 18 with a single member containing a dropping region and a labeling substance holding region having different absorbencies.

FIG. 14 is a side view showing a variation according to the present embodiment.

In the present embodiment, a fibrous material having uniformly coarse openings (namely, absorbency) in the form of a first pad 27 and a case 60 are used. The portion serving as a labeling substance holding region of the first pad 27 is pressed at a desired pressure, for example, by being housed in the case 60.

A pressing portion 613B is formed in a cover. The location of the pressing part 613B is set at a location that opposes the end portion on the downstream side of the first pad 27 (and more specifically, only the containing portion 27B) with the test kit 1D housed in the case 60. Thus, in the case the test kit 1D having the first pad 27 has been housed in the case body 62, fibers of the end portion on the downstream side of the first pad 27 are crushed by the pressing portion 613B, a difference in absorbency can be formed in the first pad 27, and a sample dropping region and a labeling substance holding region, having higher absorbency than the sample dropping region, are formed.

In the above-mentioned embodiment, production can be simplified without having to process the first pad 27 prior to incorporating into the case 60 by providing the pressing portion 613B in the case 60.

In addition, although the pressing portion 613B was formed in the cover 61 of the case 60 in the above-mentioned description, it is not limited thereto. For example, the pressing portion may also be formed protruding from the bottom of the case body 62. Moreover, restraining members and the like may be used that use a prescribed pressing force to restrain the end portion on the downstream side of the first pad 27 from above and below instead of using the case 60.

Although the preceding description has provided an explanation of several embodiments of the present invention, these embodiments are provided as examples for explaining the present invention, and it is not intended to limit the scope of the present invention to only these embodiments. The present invention can also be carried out in various other forms.

Next, an explanation of comparative experiments between the test kit according to the present invention and a test kit of the prior art is provided as Example 1.

EXAMPLE 1

The following provides an explanation of two experiments. Furthermore, a test kit for detecting type A influenza virus (substance to be detected) was used in the experiments. In addition, fluorescent polystyrene particles were used for the insoluble carrier particles serving as a label.

<<First Experiment>>

The first experiment was an experiment for comparing the developing speed of a labeling substance between a test kit according to the first embodiment and a test kit of the prior art. More specifically, the presence or absence of a labeling substance remaining near the location of a test line (which may hereinafter also be referred to as background) was evaluated at prescribed time intervals after dropping a liquid sample. In subsequent explanations of the experiments, the test kit of the prior art is explained as Test Kit A, while the test kit according to the first embodiment is explained as Test Kit B. In addition, the amount of time taken to evaluate the presence or absence of labeling substance remaining in the background is referred to as background evaluation time. The following provides a sequential explanation thereof.

<Preparation of Antibody>

Antibody preparation was carried out according to the procedure indicated below.

BALB/c mice were immunized with type A influenza virus antigen, and the spleens of the mice were removed after housing the animals for a fixed period of time followed by fusing with mouse myeloma cells to form fused cells (hybridomas).

After maintaining the fused cells (hybridomas) at a prescribed temperature, the cells were purified (monocloned) while confirming the antibody activity of the supernatant by ELISA using a plate immobilized with type A influenza virus NP antigen.

Two lines of the acquired monoclonal cells were each intraperitoneally administered to BALB/c mice followed by collecting antibody-containing ascites from each mouse after a fixed period of time.

IgG was purified from each of the resulting two types of ascites to obtain two types of purified anti-type A influenza virus NP antibodies.

<Preparation of Immobilizing Membrane>

Immobilizing membrane preparation was carried out according to the procedure indicated below.

The first anti-type A influenza virus NP antibody was diluted to a prescribed concentration with purified water.

The diluted solution was coated and dried in the form of a line at a prescribed location on a nitrocellulose membrane to form a detection zone immobilized with anti-type A influenza virus NP antibody and obtain an immobilizing membrane.

<Preparation of Labeling Substance>

Labeling substance preparation was carried out according to the procedure indicated below.

The second anti-type A influenza virus NP antibody was diluted to a prescribed concentration with purified water followed by the addition of fluorescent polystyrene particles to the diluted solution and stirring.

A crosslinking agent was further added and stirred followed by removing the supernatant by centrifugation to obtain a labeling substance (anti-type A influenza virus NP antibody-bound fluorescent polystyrene particles).

<Preparation of Labeling Substance Holding Pad>

Preparation of the labeling substance holding pad was as described below.

The labeling substance was coated onto pads (glass fiber non-woven fabric) at 2.0, 1.5, 1.2, 0.8 or 0.4 µg each followed by drying. More specifically, labeling substance holding pads (A) of the prior art, in which the labeling substance was each coated uniformly, and labeling substance holding pads (B) according to the first embodiment, which had a non-containing portion, were prepared for each of the above-mentioned pads containing five types of amounts of particles, respectively (2.0, 1.5, 1.2, 0.8 or 0.4 µg).

<Assembly of Test Kits>
Assembly of the test kits was as described below.
A kit body (immobilizing membrane, labeling substance holding pad and sample dropping pad) and an absorbent pad were arranged on the upper surface of an adhesive sheet. The arrangement of the Test Kit A of the prior art was as shown in FIG. 11 (indicated as test kit a in the drawing). The arrangement of Test Kit B of the first embodiment was as shown in FIGS. 1 and 2 (test kit 1A in the drawings).
<Preparation of Liquid Sample>
The liquid sample was prepared under prescribed conditions.
<Background Measurement>
Background measurement was carried out according to the procedure indicated below.
  50 µL of liquid sample were dropped onto the dropping pad followed by observation of the manner in which the labeling substance develops in each test kit. The labeling substance was observed visually on the immobilizing membrane.
  Observations were made at one minute intervals.
  In addition, observations were made on a transilluminator to ensure accuracy. Cases in which the labeling substance was clearly remaining were evaluated as background (+), while cases in which it was hardly visible were evaluate as background (−).
<Results>
The results are shown in Table 1.

<Preparation of Liquid Sample (Containing a Substance to be Detected)>
Preparation of the liquid sample (containing a substance to be detected) was as described below.
A solution of the substance to be detected (type A influenza virus NP antigen) was used for the undiluted liquid, and seven types of liquid samples (containing the substance to be detected) were prepared by making two-fold serial dilutions ($2^1$, $2^2$, $2^3$, $2^4$, $2^5$, $2^6$ and $2^7$).
<Measurement>
Measurement was carried out according to the procedure indicated below.
  50 µL aliquots of the above-mentioned seven types of liquid samples (containing the substance to be detected) were dropped onto Test Kit A and Test Kit B, and a determination was made as to whether or not the test line can be identified visually after a measuring time had elapsed.
  The measuring time was 8 minutes.
  In the second experiment, the following test kits in which background was evaluated as (−) at a measurement time of 8 minutes in the first experiment were evaluated. In other words, a time of 8 minutes was presumed to be the measuring time for carrying out rapid testing, and those test kits for which measuring time at which background was evaluated as (−) in the first experiment was 8 minutes or longer were excluded from evaluation.
  Test Kit A (amount of particles: 0.4 µg)
  Test Kit B (amount of particles: 0.8 µg and 1.5 µg)

TABLE 1

| Coating | Amt. of particles | Background Evaluation Time (min) | | | | | | | | | | | | | | | | | | | |
|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | 19 | 20 |
| Test Kit A (prior art) | 2 µg | + | + | + | + | + | + | + | + | + | + | + | + | + | + | + | − | − | − | − | − |
| | 1.5 µg | + | + | + | + | + | + | + | + | + | + | + | + | + | + | − | − | − | − | − | − |
| | 1.2 µg | + | + | + | + | + | + | + | + | + | + | + | + | + | − | − | − | − | − | − | − |
| | 0.8 µg | + | + | + | + | + | + | + | + | + | + | + | + | − | − | − | − | − | − | − | − |
| | 0.4 µg | + | + | + | + | − | − | − | − | − | − | − | − | − | − | − | − | − | − | − | − |
| Test Kit B | 2 µg | + | + | + | + | + | + | + | + | − | − | − | − | − | − | − | − | − | − | − | − |
| | 1.5 µg | + | + | + | + | + | + | − | − | − | − | − | − | − | − | − | − | − | − | − | − |
| | 1.2 µg | + | + | + | + | + | − | − | − | − | − | − | − | − | − | − | − | − | − | − | − |
| | 0.8 µg | + | + | + | + | − | − | − | − | − | − | − | − | − | − | − | − | − | − | − | − |
| | 0.4 µg | + | − | − | − | − | − | − | − | − | − | − | − | − | − | − | − | − | − | − | − |

The amount of particles held in the labeling substance holding pad of Test Kit B was evaluated as background (−) in a shorter period of time in comparison with Test Kit A in all cases. In other words, it was determined from the present experiment that Test Kit B allows the labeling substance to be developed more rapidly than Test Kit A regardless of the amount of labeling substance held in the labeling substance holding pad. From a different perspective, Test Kit B was determined to allow the loading of a larger amount of the labeling substance than Test Kit A in the comparatively short evaluation time of 8 to 10 minutes after dropping.
<<Second Experiment>>
It was determined from the first experiment that the Test Kit B enables a liquid sample containing a labeling substance to develop more rapidly than the Test Kit A. However, even if development is rapid, an accurate evaluation cannot be made unless there is favorable sensitivity. The second experiment was an experiment for comparing the labeling substance sensitivity of a test kit according to the first embodiment and a test kit of the prior art. The following provides a sequential explanation thereof.

In addition, observations were made on a transilluminator to ensure accuracy. Cases in which labeling of the test line was able to be identified visually were evaluated as test line (+), while cases in which labeling of the test line was unable to be identified were evaluated as test line (−).
<Results>
The results are shown in Table 2.

TABLE 2

| | Amt. of | Flu A Type Sensitivity Test Serial Dilution | | | | | | |
|---|---|---|---|---|---|---|---|---|
| Coating | Particles | $2^1$ | $2^2$ | $2^3$ | $2^4$ | $2^5$ | $2^6$ | $2^7$ |
| Test Kit A | 0.4 µg | + | + | + | + | − | − | − |
| Test Kit B | 1.5 µg | + | + | + | + | + | + | − |
| | 0.8 µg | + | + | + | + | + | − | − |

The above-mentioned evaluation consisted of evaluating the test line 8 minutes after dropping the liquid sample (containing the substance to be detected) onto each test kit. The dilution factor of liquid samples (containing the substance to be detected) the substance evaluated as test line (+) was higher for Test Kit B in comparison with Test Kit A. In Test Kit B having a labeling substance holding pad in which the amount of particles was 1.5 µg in particular, labeling of the test line was able to be identified even when using a liquid sample (containing the substance to be detected) having a high dilution factor of $2^6$. In other words, in the present experiment, Test Kit B was determined to have high sensitivity in comparison with Test Kit A at the comparatively short time after dropping of 8 minutes.

According to the above-mentioned first and second experiments, Test Kit B was determined to enable detection of a substance to be detected both faster and with higher sensitivity in comparison with Test Kit A.

REFERENCE SIGNS LIST

1A Test kit
10A Kit body
11 Sample dropping pad
13 Labeling substance holding pad
13a Non-containing portion
13b Containing portion
15 Immobilizing membrane
20 Absorbent pad
30 Sheet

The invention claimed is:

1. A test kit for detecting a substance to be detected contained in a liquid sample by allowing the liquid sample to develop in a developing direction, the test kit comprising:
   a dropping region, which contains a portion onto which the liquid sample drops;
   a labeling substance holding region including a non-containing portion connected downstream of the dropping region in the developing direction, and including a containing portion containing a labeling substance with a label immobilized on a substance that specifically binds with the substance to be detected is held;
   a developing region, which has a detection zone where the labeling substance is captured through the substance to be detected, at least a portion of which is connected downstream of the labeling substance holding region in the developing direction, and which allows the labeling substance having been made to flow out from the labeling substance holding region by the liquid sample, to develop into the detection zone; and
   retention inhibition means for inhibiting retention of the labeling substance in the labeling substance holding region when the liquid sample develops downstream, the retention inhibition means configured such that:
      the non-containing portion not containing the labeling substance is arranged in a furthermost upstream portion of the labeling substance holding region;
      the dropping region is further connected to the labeling substance holding region only through the non-containing portion; and
      the developing region is connected to the labeling substance holding region only through the containing portion, wherein the containing portion ends where the developing region begins.

2. The test kit according to claim 1, further comprising backflow inhibiting means for inhibiting the liquid sample containing the labeling substance from flowing back from a downstream region in the developing direction to an adjacent upstream region in the developing direction.

3. The test kit according to claim 2, wherein, in the backflow inhibiting means, the absorbency of the downstream region in the developing direction is set higher than the absorbency of the upstream region in the developing direction.

4. The test kit according to claim 2, wherein the backflow inhibiting means is provided between the labeling substance holding region and the dropping region.

5. The test kit according to claim 1, wherein the non-containing portion absorbency is uniform.

6. The test kit according to claim 1, wherein the retention inhibiting means is configured such that an end surface of the dropping region on the downstream side is further connected to an end surface of the non-containing portion on the upstream side.

7. The test kit according to claim 6, wherein the dropping region and the labeling substance holding region are integrally formed by a single member.

8. The test kit according to claim 7, wherein the single member is a fibrous member having uniform absorbency, and the labeling substance holding region is formed by pressing a portion serving as the labeling substance holding region.

9. The test kit according to claim 1, wherein the labeling substance holding region is formed of only a containing portion containing the labeling substance, and the retention inhibiting means is configured such that an end surface of the dropping region on the downstream side is connected to an end surface of the labeling substance holding region on the upstream side.

10. The test kit according to claim 9, wherein the dropping region and the labeling substance holding region are integrally formed by a single member.

11. The test kit according to claim 10, wherein the single member is a fibrous member having uniform absorbency, and the labeling substance holding region is formed by pressing a portion serving as the labeling substance holding region.

12. The test kit according to claim 1, wherein the absorbency of the labeling substance holding region is uniform.

13. The test kit according to claim 1, wherein the labeling substances are uniformly held in the containing portion.

14. The test kit according to claim 1, wherein the containing portion is arranged only to contact the upper surface of the developing region.

15. A test kit for detecting a substance to be detected contained in a liquid sample by allowing the liquid sample to develop in a developing direction, the test kit comprising:
   a dropping region, which contains a portion onto which the liquid sample drops;
   a labeling substance holding region including a non-containing portion connected downstream of the dropping region in the developing direction, and including a containing portion containing a labeling substance with a label immobilized on a substance that specifically binds with the substance to be detected is held;
   a developing region, which has a detection zone where the labeling substance is captured through the substance to be detected, at least a portion of which is connected downstream of the labeling substance holding region in the developing direction, and which allows the labeling substance having been made to flow out from the labeling substance holding region by the liquid sample, to develop into the detection zone, wherein:
      the absorbency of the labeling substance holding region is set higher than the absorbency of the dropping region;

the non-containing portion that does not contain the labeling substance is provided in a furthermost upstream portion of the labeling substance holding region; and the dropping region is further connected to the labeling substance holding region only through the non-containing portion; and the developing region is connected to the labeling substance holding region only through the containing portion, wherein the containing portion ends where the developing region begins.

16. A test kit for detecting a substance to be detected contained in a liquid sample by allowing the liquid sample to develop in a developing direction, the test kit comprising:

a dropping region, which contains a portion onto which the liquid sample drops;

a labeling substance holding region including a non-containing portion connected downstream of the dropping region in the developing direction, and including a containing portion in which a labeling substance with a label immobilized on a substance that specifically binds with the substance to be detected is held; and a developing region, which has a detection zone where the labeling substance is captured through the substance to be detected, at least a portion of which is connected downstream of the containing portion of the labeling substance holding region in the developing direction, and which allows the labeling substance having been made to flow out from the labeling substance holding region by the liquid sample, to develop into the detection zone, wherein:

the absorbency of the labeling substance holding region is set higher than the absorbency of the dropping region;

an end surface of the dropping region on the downstream side is connected only to an end surface of the non-containing portion of the labeling substance holding region on the upstream side; and a beginning surface of the developing region on the upstream side is connected only to a downstream surface of the containing portion of the labeling substance region on the downstream side, wherein the containing portion of the labeling substance region ends where the developing region begins.

* * * * *